United States Patent [19]
Hedberg et al.

[11] Patent Number: 5,396,285
[45] Date of Patent: Mar. 7, 1995

[54] ULTRASOUND IMAGING METHOD AND APPARATUS WITH DYNAMIC NON-LINEAR FILTERING

[75] Inventors: Dave Hedberg, Menlo Park; Ismayil M. Guracar, Redwood City; Michael J. Tierney, Pleasanton; Stuart Carp, Menlo Park; James W. Arenson; Samuel H. Maslak, both of Woodside, all of Calif.

[73] Assignee: Acuson Corporation, Mountain View, Calif.

[21] Appl. No.: 60,204

[22] Filed: May 7, 1993

[51] Int. Cl.$^6$ ............................................. H04N 7/18
[52] U.S. Cl. ...................................... 348/163; 73/602; 128/660.04
[58] Field of Search ................... 358/112; 348/163; 73/602; 128/660.01, 660.04, 660.05; H04N 7/18

[56] References Cited

U.S. PATENT DOCUMENTS

| | | | |
|---|---|---|---|
| 4,212,072 | 7/1980 | Huelsman et al. | 358/112 |
| 4,581,636 | 4/1986 | Blaker et al. | 358/112 |
| 4,751,846 | 6/1988 | Dousse | 358/112 |
| 4,783,839 | 11/1988 | Bamber | 358/112 |

*Primary Examiner*—Howard W. Britton

[57] ABSTRACT

Methods and apparatus for enhancing the clarity of and the diagnostic information in real-time B-mode and M-mode ultrasound displays including a beamformer for acquiring ultrasound receive signals for each ultrasound scan line of a two-dimensional image and processing the receive signals for each ultrasound scan line into detected and filtered video signals for storage in scan line acquisition memory with programmable dynamically variable non-linear filters for processing the video signals with continuously and automatically varying filter responses over a range of low and high pass responses followed by scan converting and display of the non-linearly processed video signals. The non-linear filters may process video signals in range along each ultrasound scan line or azimuthally along multiple ultrasound scan lines of a two-dimensional B-mode image. The non-linear filters also can be two-dimensionally programmable for processing video signals both in range along each ultrasound scan line and azimuthally along multiple ultrasound scan lines over regions of a two-dimensional B-mode image. The non-linear filter may be responsive to a local signal measurement and to spatial positions in a B-mode image for control of filter parameters. The non-linear filter can also be programmable to accommodate variable system characteristics for particular imaging applications.

14 Claims, 12 Drawing Sheets

$$\begin{bmatrix} \dfrac{-(\alpha_1+\alpha_2)}{2} & -\alpha_1 & \dfrac{-(\alpha_1+\alpha_2)}{2} \\ \\ -\alpha_2 & 1+4\alpha_1+4\alpha_2 & -\alpha_2 \\ \\ \dfrac{-(\alpha_1+\alpha_2)}{2} & -\alpha_1 & \dfrac{-(\alpha_1+\alpha_2)}{2} \end{bmatrix}$$

VIDEO RESPONSE FAMILY, 0.8 Mhz, 440 ns, a = −0.3 TO 0.4

ULTRASOUND IMAGING METHOD AND APPARATUS WITH DYNAMIC NON-LINEAR FILTERING

BACKGROUND OF THE INVENTION

The receive signal processing path for an ultrasound imaging system processes signal information received from the beamformer for each acquired ultrasound scan line, typically with log amplification, envelope detection, and low pass video filtering prior to scan conversion and display. While video filtering objectives may be many, the filtering is typically done with a linear-phase low pass filter in order to limit noise and to shape the frequency response of the signal for display without significant spatial distortion. Typical requirements are that the video filters do not contribute group delay distortion in the passband where there is significant signal energy and that the filter response and bandwidth are approximately matched to the spectral characteristics of the transducer and system in each particular imaging mode.

The video path response is often varied using selectable filters in order to provide either smoother or sharper (i.e. crisper) looking edge detail in the image. For example, the video path may use a linear-phase filter with Gaussian-like magnitude response together with a selectable FIR high pass filter to "whiten" or "sharpen" the imaging frequency response. These filters can be set to make the image look more focused on edges and with higher contrast edge detail. Such filters may be used in combination with other enhancement filters and with a nonlinear mapping of video intensities in order to suppress the low level noise, improve contrast, and improve the dynamic range presentation of ultrasound images on the display.

The use of two-dimensional linear FIR "enhancement" filters on the detected scan data has been mentioned in the prior art for ultrasound systems. Such filters would typically be implemented in the signal path following scan line data accumulation memories and prior to scan conversion. The objectives of the two-dimensional image filtering can be many, including provisions for either smoother or sharper (i.e. crisper) looking edge detail in the image or to suppress noise tendencies in the speckle-like tissue regions at lower grey levels. The two-dimensional FIR filter may be implemented as a cascade of independent azimuth and range filters (i.e. separable form) or as a nonseparable two dimensional FIR kernel. Typical objectives are that the two-dimensional filter frequency response characteristics be approximately matched to the spectral characteristics of the transducer and system in a particular imaging mode to provide a "whitened" composite imaging response.

For the range coordinate, the resulting filtered signal spectrum is determined by the receive detected signal spectral characteristics resulting from transducer and system response. The system response includes the fixed video filters in the path, and the contribution of the two-dimensional FIR filter response. For the azimuthal coordinate, the filtered signal spectrum is determined by the sampled azimuthal signal resulting from the scanning process, the scan line density and azimuthal beam profile, and the azimuthal component of the two-dimensional FIR filter response. If a nonseparable filter kernel is used, the resulting spatial spectrum along a given direction will depend on the full two-dimensional frequency response contributors of image, transducer, beam point spread function, and other system response parameters.

The two-dimensional response of the video path is often varied using selectable filter tap spacings, line spacings, and tap weightings to provide either smoother or sharper (i.e. crisper) looking edge detail in the image. Low pass smoothing FIR filter responses can be used to smooth out speckle and make tissues look more uniform in contrast.

Heretofore, ultrasound video range filtering implementations have been restricted to selectable linear filters which have pre-determined frequency responses with different bandwidths. The different filter responses are typically set by the system operator. Some systems may have filters with gradual low pass response rolloff for restricting bandwidth or smoothing the image characteristics. Due to these filter limitations conventional ultrasound systems do not have the flexibility to optimize response for a wide range of transducer and imaging conditions.

Accentuation of background noise and the degradation of contrast resolution of subtle tissue textures and tissue-structural interfaces is a limitation in any linear image filter implementation that attempts to increase local contrast and sharpen the appearance of an image because, with linear filters, background noise and tissue speckle is enhanced to the same degree as structural interfaces.

The use of smoothing filter responses reduces noise and improves subtle tissue contrast uniformity, but at the expense of loss of edge detail and a duller looking image. Again, with linear filters, smoothing is accomplished for all signals—low level noise as well as strong signals with structural details that do not benefit from smoothing. Noise can be reduced by other methods such as temporal filtering, but in that case, not without some degradation of the temporal signal response.

Similarly, two-dimensional filtering implementations are typically very simple and restricted to selectable linear filters, cascaded range and azimuth filters (i.e. separable implementations), which have pre-determined frequency responses with different bandwidths. The different filter responses are typically set by the system operator or by the system software in conjunction with the scanning and scan conversion mode. Azimuthal filter sample spacing is typically fixed.

The accentuation of background noise and the degradation of contrast resolution of subtle tissue textures and tissue-structural interfaces is a limitation of any two-dimensional linear filtering scheme, too, which attempts to increase local contrast in both dimensions and thereby sharpen the appearance of an image. The use of smoothing filter responses reduces noise and improves subtle tissue textures, but at the expense of loss of edge detail, and contrast, resulting in a duller looking image.

In separable two-dimensional filter implementations which use, strong high pass responses on both axes, the axial and azimuthal edge response will be enhanced while the diagonal edge frequency response will be smoothed making the total response behavior sensitive to the orientation of edge detail.

SUMMARY OF THE INVENTION

This invention includes apparatus and methods for processing ultrasound signals to provide increased image clarity and additional diagnostic information from two-dimensional B-scan images using dynamic non-linear analog or digital signal processing in one dimension (i.e. range filtering along an ultrasound scan line) and dynamic non-linear signal processing in two-dimensions (i.e. azimuthal and range filtering of the B-mode image.) The innovations consist of several parts which may be used together or independently. These include a digitally programmable non-linear range filter for processing along an ultrasound scan line, an azimuthal filter with similar characteristics for processing in azimuth along several ultrasound scan lines within the scan field, a full two-dimensional digitally programmable nonlinear filter for processing local regions of the two-dimensional B-mode image scan data, means for programming the non-linear characteristics of the filters, and means of selecting filter families and parameters under software control. The use of local signal measurements and spatial position to control the filter parameters are also aspects of the innovations.

A set of one dimensional range filters may be implemented in the receive signal processing path either prior to scan line data accumulation and/or in the path following scan line data accumulation and prior to scan conversion. If the beamformer is analog, the range filter may be a digitally programmed analog filter prior to A/D conversion. A set of one or two-dimensional digital range and azimuth filters may be implemented in the receive signal processing path following the line acquisition memories and prior to scan conversion. The techniques and digital filter configurations are applicable with analog beamformers or digital beamformers.

DESCRIPTION OF THE INVENTION

Figure 1:
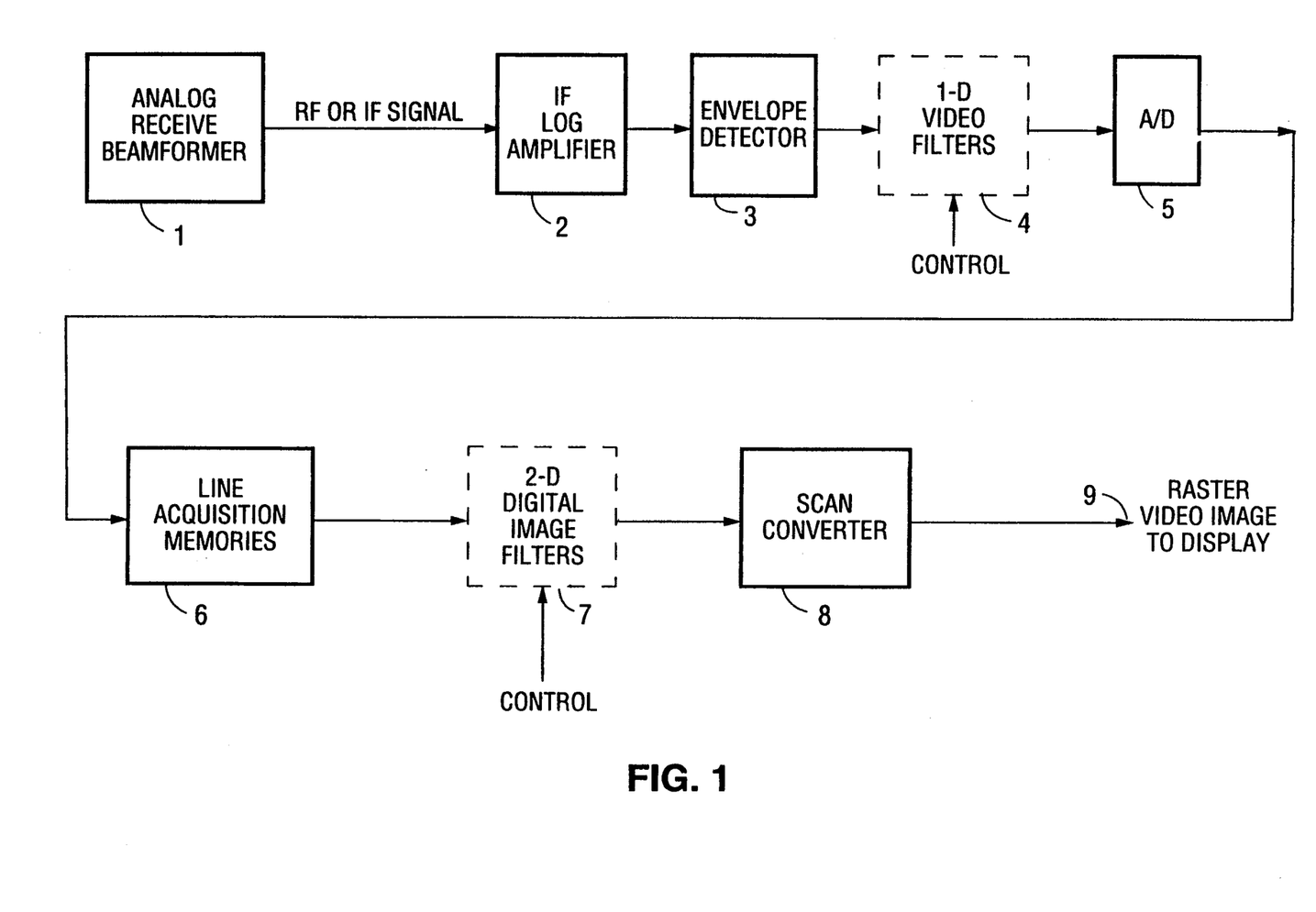
FIG. 1 is a schematic block diagram of the receive processing path of an ultrasound imaging system.

FIG. 1 illustrates a typical ultrasound receive signal processing path implemented by an analog receive beamformer 1. Coherent receive signals at RF or IF are applied to a log amplifier 2 and envelope detector 3 to generate video output signals for each ultrasound scan line. One-dimensional video filters 4 process the video signals for each ultrasound scan line as described in the background of this invention or with the programmable non-linear filters that are part of this invention. The filtered analog signals are converted in A/D converter 5 to digital format and are stored in line acquisition memories 6 for each ultrasound scan line. Two-dimensional digital image filters 7 process the digital signals prior to input to scan converter 8 for a raster output format for video monitor display as at 9. The two-dimensional digital image filters 7 may be as described in the prior art or may be the programmable non-linear digital filters implemented by this invention.

Figure 2:
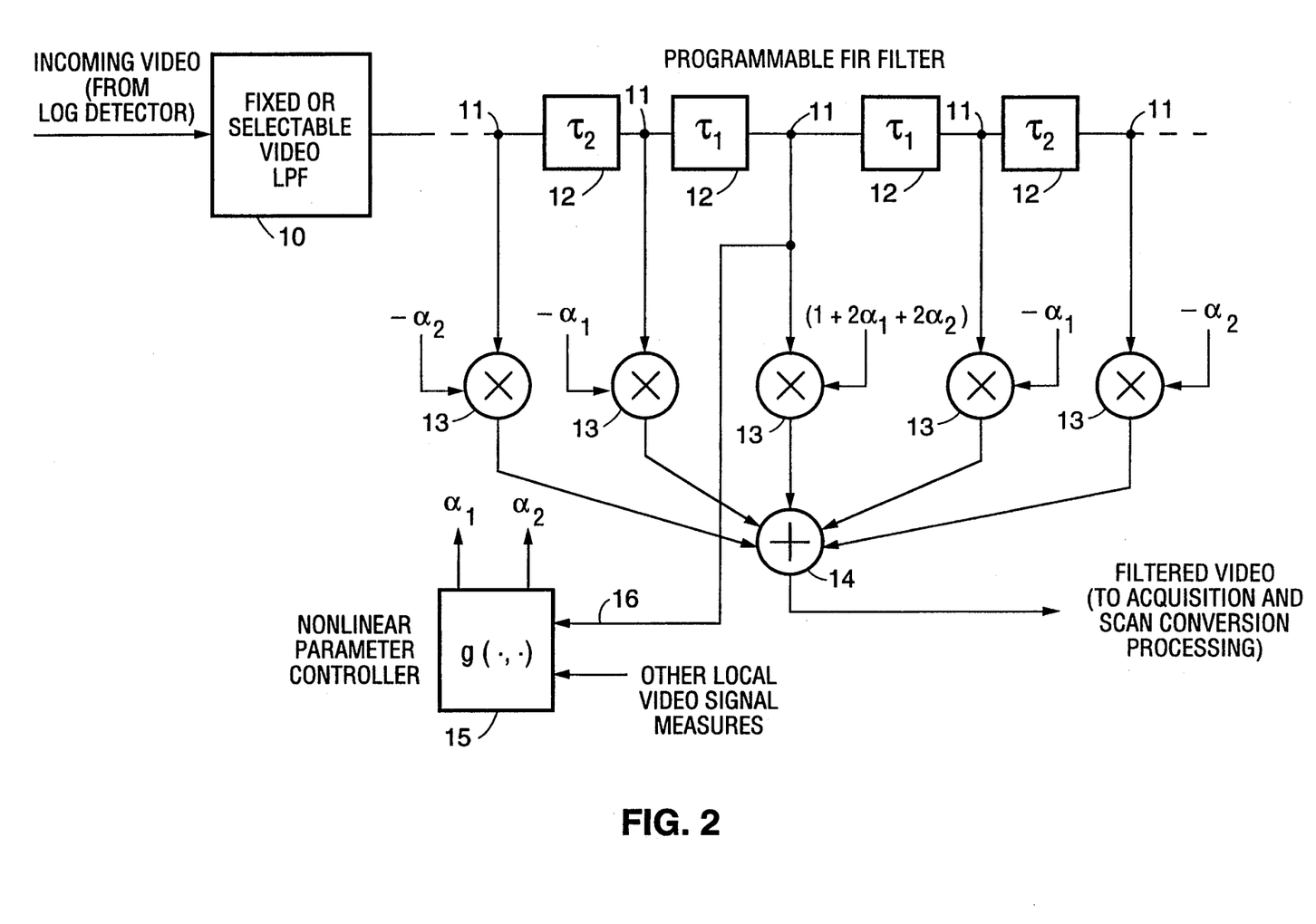
FIG. 2 is a functional block diagram of the general structure of a programmable non-linear video range filter of this invention.

The general structure of a one dimensional dynamic non-linear range filter 4 of this invention is shown in FIG. 2. Although this architecture may be implemented for either analog or digitized signal paths, the circuit implementation described is for an analog signal path. The filter structure comprises selectable fixed low pass filter sections and a variable FIR filter section which can be varied from low pass through high pass responses. Although the five-tap FIR structure shown is a conventional linear type, the linear summation operations could be replaced by more general nonlinear combining operations to yield additional response flexibility. The later is particularly attractive in a digital implementation of the filter.

The illustrated filter structure is programmable in the sense that the fixed and programmable FIR sections with different tap spacing characteristics can be selected automatically to achieve the family of responses desired to match a particular transducer and system operating mode. FIG. 2 shows incoming video signals from log detector 2, 3—of FIG. 1, passed through a low pass filter 10 to a two parameter ($\alpha_1$, $\alpha_2$) symmetric, five-tap linear phase FIR filter normalized for unity gain. The five taps 11 at filter delays 12 each connect to one of multipliers 13 for combination with a selected one of parameters, $\alpha_1$, $\alpha_2$ with the products added at summer 14. Other FIR filter configurations can equally serve this technique. The number and spacings of the FIR filter taps and delays 11, 12 are chosen in a particular design to match the range of responses desired for a particular transducer and particular imaging mode.

One of the key image enhancement capabilities derives from use of a non-linear filter parameter controller 15 which is driven by a local image signal value at 16 so that the filter can vary its characteristics dynamically based on the local signal level. The filter parameter controller 15 is programmable in order to tailor its non-linear control characteristics to the imaging mode objectives.

The described new general filter structure provides many features:

Families of frequency responses programmed over a wide range of linear phase response characteristics. (based on the requirements of the transducer and imaging mode).

The composite filter structure can be inherently linear phase in the passband and has a low pass nature with a stopband in order to reject out-of-band noise or low or high frequency signal components. The linear phase nature of the filter eliminates concerns about introducing spatial distortion in the image.

The response characteristics and effective bandwidth can be continuously and instantaneously varied over a wide range (e.g. greater than 5:1) without introducing unwanted control transients.

With a fixed control parameter input, the filter sections do not alter the average image signal intensity but do alter the local contrast such as to enhance or smooth edge detail. The contrast enhancement characteristics are frequency selective.

The filter can be made dynamically nonlinear by varying the response control parameters based on a local measure of the image signal. (e.g. the local intensity).

The nonlinear action can be programmed over a wide range of characteristics. (Based on the objectives of the imaging application mode).

The composite filter can be programmed in order to overcome the disadvantages of conventional filters. Namely, background noise can be reduced and contrast resolution of subtle tissue textures can be preserved while simultaneously preserving edge detail and a sharp looking image for high contrast details.

Conventional linear filters applicable to ultrasound imaging are a subset of this more general filter structure.

The filter is inherently an intraframe filter and introduces no temporal distortion, although it could be used constructively in conjunction with interframe filters.

The filter structure is amenable to cost effective analog and digital hardware implementations.

A digital implementation of the dynamic non-linear range filter provides a greater level of flexibility for additional filter functions using the same general principle as described in connection with FIGS. 4-6. The use of a digital dynamic non-linear range filter in the system assumes the presence of fixed or selectable video low pass filters in the receive signal path as shown in FIGS. 1 and 2. However, instead of the programmable FIR filter section shown in FIG. 2, there is a more general filter structure which can be implemented with a digital circuit following the analog-to digital converter 5 and line accumulation memory 6.

Two-dimensional filtering is achieved with a cascade of the one-dimensional dynamic non-linear range filter described and a digital azimuth filter which also utilizes the dynamic non-linear processing technique. If both filters are operated in the dynamic non-linear mode, then the ordering of the two filters in the cascade can make a difference in overall response. We assume that the azimuthal filter precedes the range filter in the generic signal path of FIG. 1. Alternatively, dynamic non-linear 2-dimensional filtering can be implemented using a non separable 2-D FIR kernel based filter.

An ultrasound image can be smoothed or sharpened by filtering the detected ultrasound signal. Smoothing can be accomplished by providing some amount of low pass filtering, and sharpening can be accomplished by providing some high pass filtering or peaking. Since the spectrum of the detected ultrasound signal depends on a number of variables (including transducer bandwidth, operating frequency, transmit spectrum, receiver bandwidth, detector characteristics, and attenuation in the body), there is a no single high pass or low pass filter that will work for all operating conditions. However, the bandwidth of the detected ultrasound signal can be calculated or measured for the expected operating conditions, thereby determining the correct part of the signal spectrum that needs either suppression (for smoothing) or enhancement (for sharpening). Through the selection of the correct tap spacings and coefficient weights, a family or set of fixed or linear filters can be determined to match the particular operating conditions. These filter operating parameters are controlled by microcode specific to the transducer and system operating condition.

Figure 12:
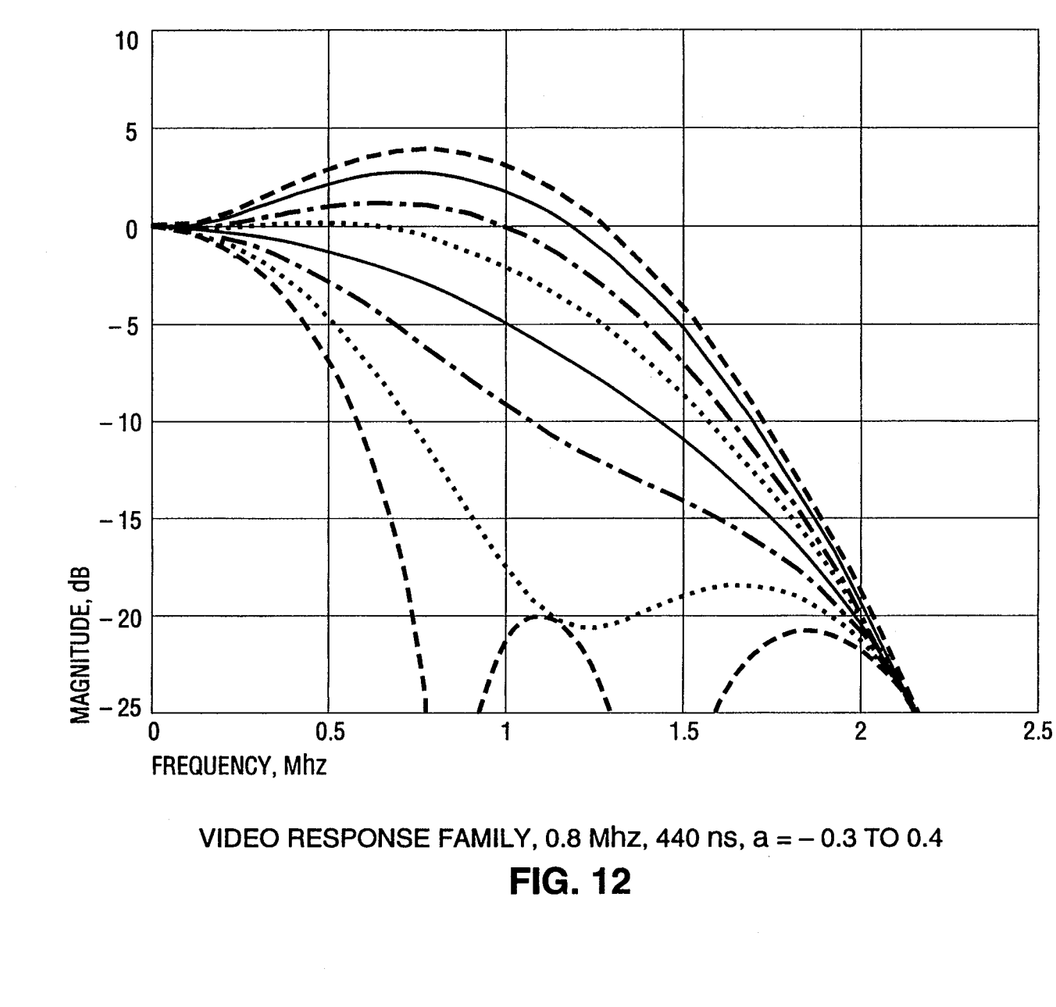
FIG. 12 depicts a family of response characteristics that can be realized with this invention.

The fixed filters served as an operating point about which the non-linear filters can operate. For example, once a fixed filter for maximal smoothing has been determined, then this can be used as the lower limit for the non-linear filter operation. The upper limit of this non-linear filter can be set to match the next sharper fixed filter in the linear filter family. In a similar way, a family of non-linear filters can be determined. FIG. 12 shows a typical family of responses realizable with a 3 tap filter.

In some applications a wider range of non-linear operation may be required, where the range of operation covers more than one fixed filter step. In this case one may find that a non-linear filter provides smoothing for low level signals, while providing sharpening for high level signals.

In all these cases, the user selects the appropriate filter by some switch means that causes the system software to select and cycle through the filters in the family.

FIG. 11 shows a series of time response signals. FIG. 11A illustrates a typical A-mode scan line, where 21 represents noise and clutter in the image, 22 represents the signal from a bright target, and 23 represents the signal from a less bright target.

Figure 11A:
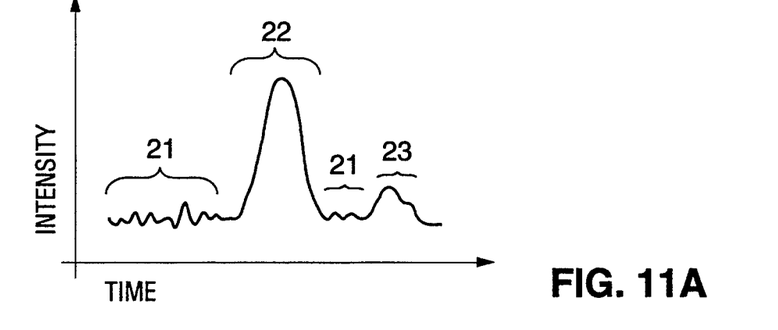
FIG. 11 illustrates a series of time response signals.
Figure 11B:
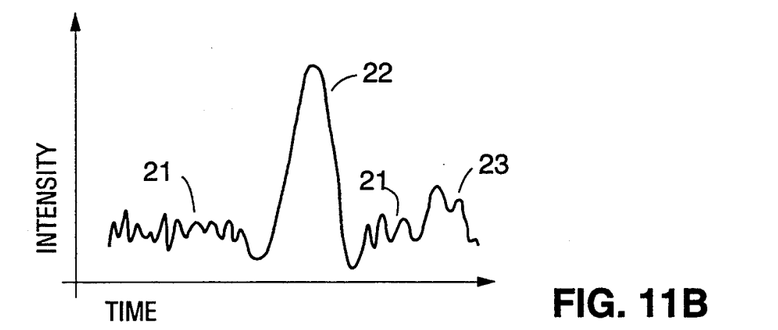

FIG. 11B demonstrates the resulting A-mode scan signal after filtering by a conventional linear filter. Both clutter and signal are enhanced, and the less bright target can be difficult to see amid the enhanced clutter.

Figure 11C:
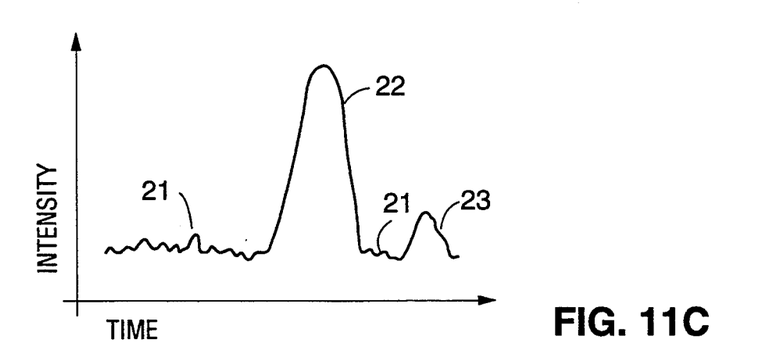

FIG. 11C demonstrates the resulting A-mode signal after non-linear filtering. This example offers no smoothing, only increased sharpening with increased signal strength. It is clear here that the clutter level is not affected, while the signal from both the bright target and the less bright target are enhanced.

Figure 11D:
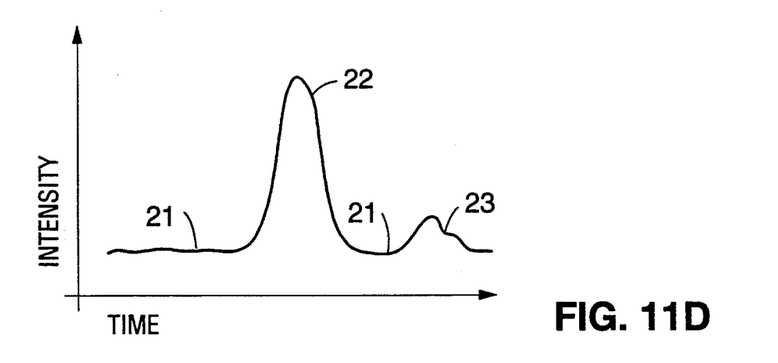

FIG. 11D demonstrates the resulting A-mode signal after non-linear filtering. In this example some smoothing is done for low level signals, and sharpening is done for higher level signals. The figure demonstrates that clutter can be reduced by smoothing while still providing sharpening for higher level signals.

Figure 3:
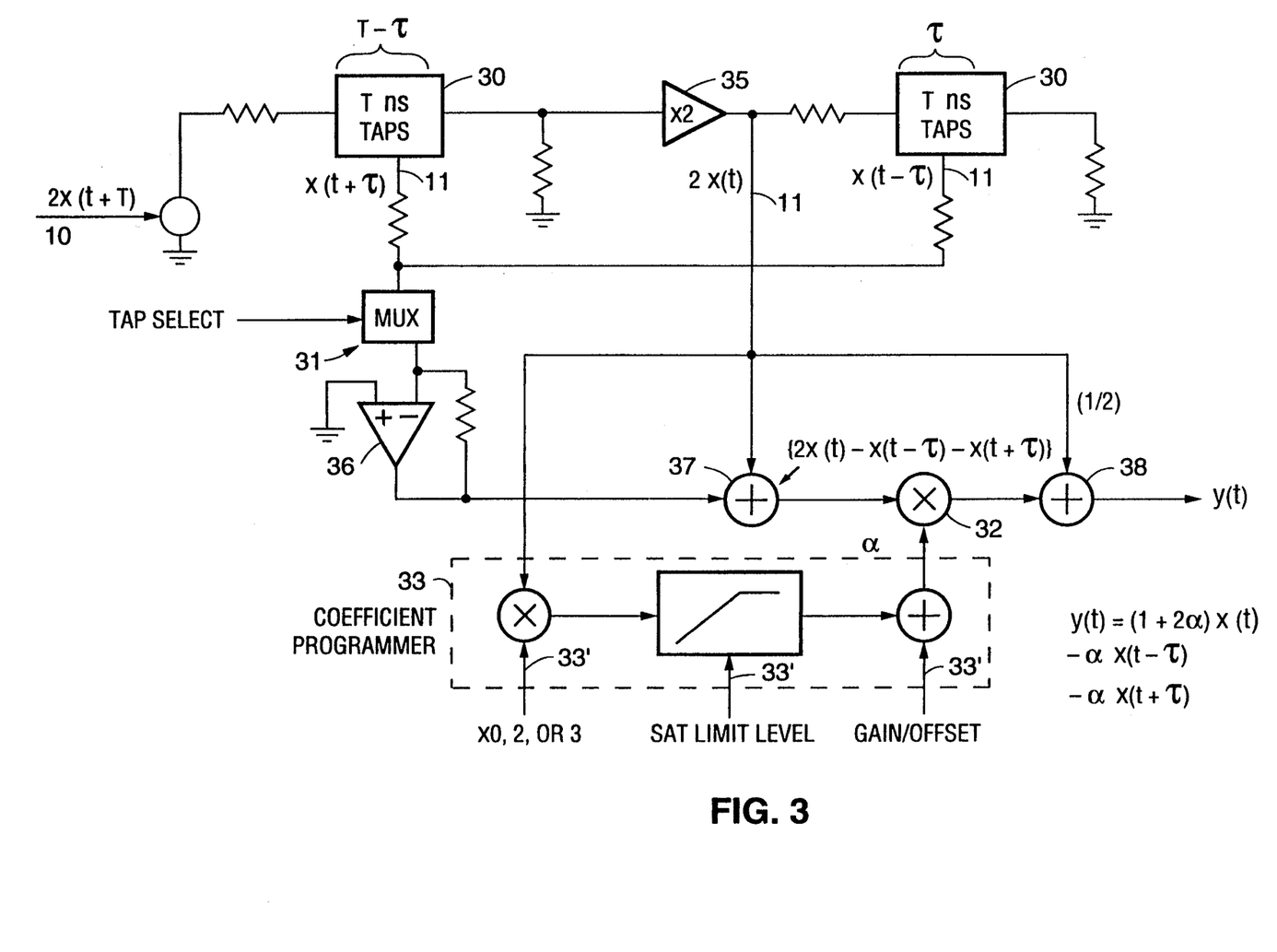
FIG. 3 is a simplified schematic diagram of a programmable non-linear range filter of this invention for an analog signal path.

A preferred embodiment of the filter for an analog signal path is shown in the simplified schematic diagram of FIG. 3. The diagram shows a one parameter variable 3-tap FIR implementation and the non-linear analog elements associated with this filter. Such analog filters can be implemented with high performance using tapped passive delay lines 30 which are terminated in their characteristic line impedance. High impedance intermediate taps can be multiplexed by tap selector 31 in order to provide for programmability under software control of the tap spacings (and consequently programmability of the family of video responses to be selected). This is important in an ultrasound system in order to match filter characteristics to a wide range of transducer applications which could for example include RF imaging frequencies from 2.0 to 7.0 MHz. Since the FIR tap weightings are symmetrical (a requirement for linear phase filters), a 3-tap filter requires only one analog multiplier 32 which can be shared for all modes. The nonlinear controller elements are shown in the coefficient programmer 33 and these are also shared for all programmable modes. The non-linear controller parameters indicated are also fully programmable under software control. The analog control parameters 33' are generated by means of D/A converters.

In FIG. 3 the input video signal enters at the left from detector/low pass videos filter 10. The signal is delayed by two cascaded double terminated passive tapped delay lines 30. An amplifier 35 between the delay lines 30 makes up for voltage losses in the lines and terminations. The three relatively time delayed signals required for the filter are derived from the center tap 11 and the two intermediate taps 11. Tap spacing selection is implemented by means of an analog switch 31. Although only one tap pair is shown, the technique is used with several analog switches, one or more of which are turned on at a time. The outputs of the switches are connected to a set of summing nodes when turned on or they are connected to ground when not turned on. In either case, the intermediate tap loadings on the passive delay lines are the same.

The diagram shows only one summing inverting amplifier 36 which produces the summed outer tap terms for the 3 tap FIR filter that is illustrated. The weighted center tap signal 2x(t) and the selected outer tap terms $x(t\tau)$ and $x(t+\tau)$ can be summed at summer 37 and then input to the analog multiplier 32. Since the filter must be capable of wideband realtime nonlinear filtering without distortion, the summing amplifiers and 4-quadrant analog multiplier must be wideband designs such as achievable with Gilbert cell analog multiplier technology. The topology described here is amenable to simple and cost effective implementations since all of the arithmetic processing required can be done with one summing amplifier IC, one analog multiplier IC, and several resistors. The output of the multiplier is equivalent to the difference signal between input and output. Thus, to produce the final filtered output, only the center tap signal voltage needs to be summed with this voltage at summer 38.

The illustrated analog filter of FIG. 3 is configured to vary the FIR filter response continuously between smoothing responses, corresponding to negative values of the filter parameter, $\alpha$, and sharpening responses corresponding to positive values of $\alpha$. The DC gain of the filter is independent of $\alpha$. A typical family of responses is given in FIG. 12. When in the nonlinear mode, the video signal increases the filter bandwidth dynamically as the video level increases until an upper limit in bandwidth is reached. Beyond that level, the filter bandwidth and response remains fixed. The rate at which the video signal increases the bandwidth is programmable with weightings of x1, x2, or x3. The initial response and bandwidth corresponding to zero video level is programmable via the gain/offset input. The net effect of the nonlinear mode of operation is to smooth signals with lower average video gray levels and to sharpen edges and enhance contrast in higher level signals. The transition behavior between these two extremes is continuously dependent on the intermediate video levels.

The nonlinear operation of the filter of FIG. 3 is achieved by weighting the center tap signal, limiting its upper level with a clipping circuit, and then summing in an offset term to set the range of the filter parameter action. The resulting signal represents the variable filter parameter control input to the multiplier 32. All of the nonlinear controller elements are implemented with simple analog circuits having negligible delay. The example shows only one case of possible analog programmable nonlinear controllers and their cost effectiveness.

Innovations in the analog circuit of FIG. 3 include the technique for generating multiple high quality delayed signals over a wide delay range for programmable analog FIRs; for wideband tap spacing selections using analog switches; for minimizing the number of analog multipliers required; for making filter DC gain independent of tap selection and independent of the filter response parameter; for allowing accurate, continuous, and instantaneous variation of the filter response under analog and digital programming control; for achieving programmable non-linear dynamic bandwith operation; and for allowing the analog processing circuits for these capabilities to be shared over a wide range of programmable filter families, providing usable characteristics over the full range of ultrasound signal bandwidths.

Figure 4:
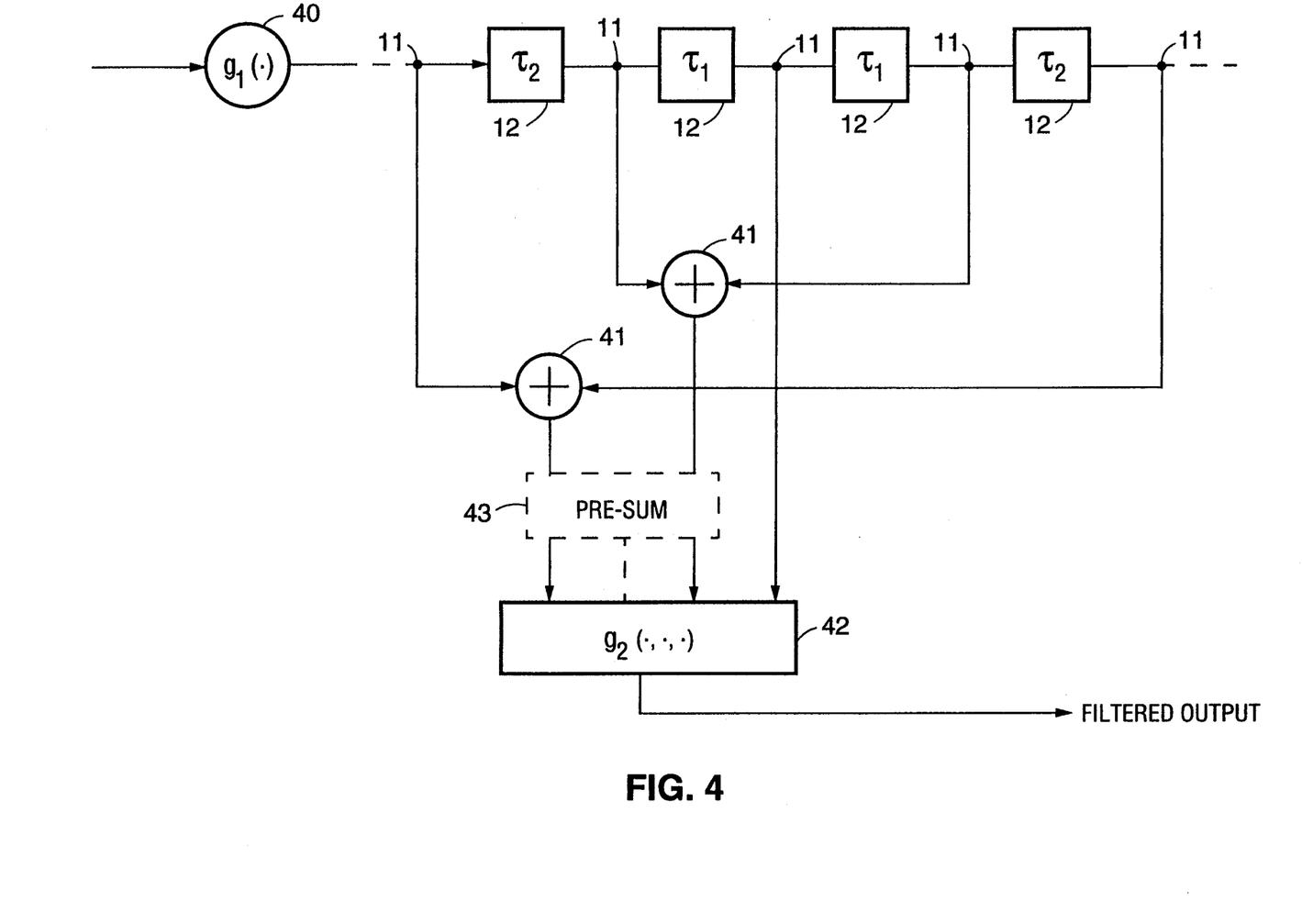
FIG. 4 is a functional block diagram for a programmable non-linear range filter of this invention for a digital signal path.
Figure 5:
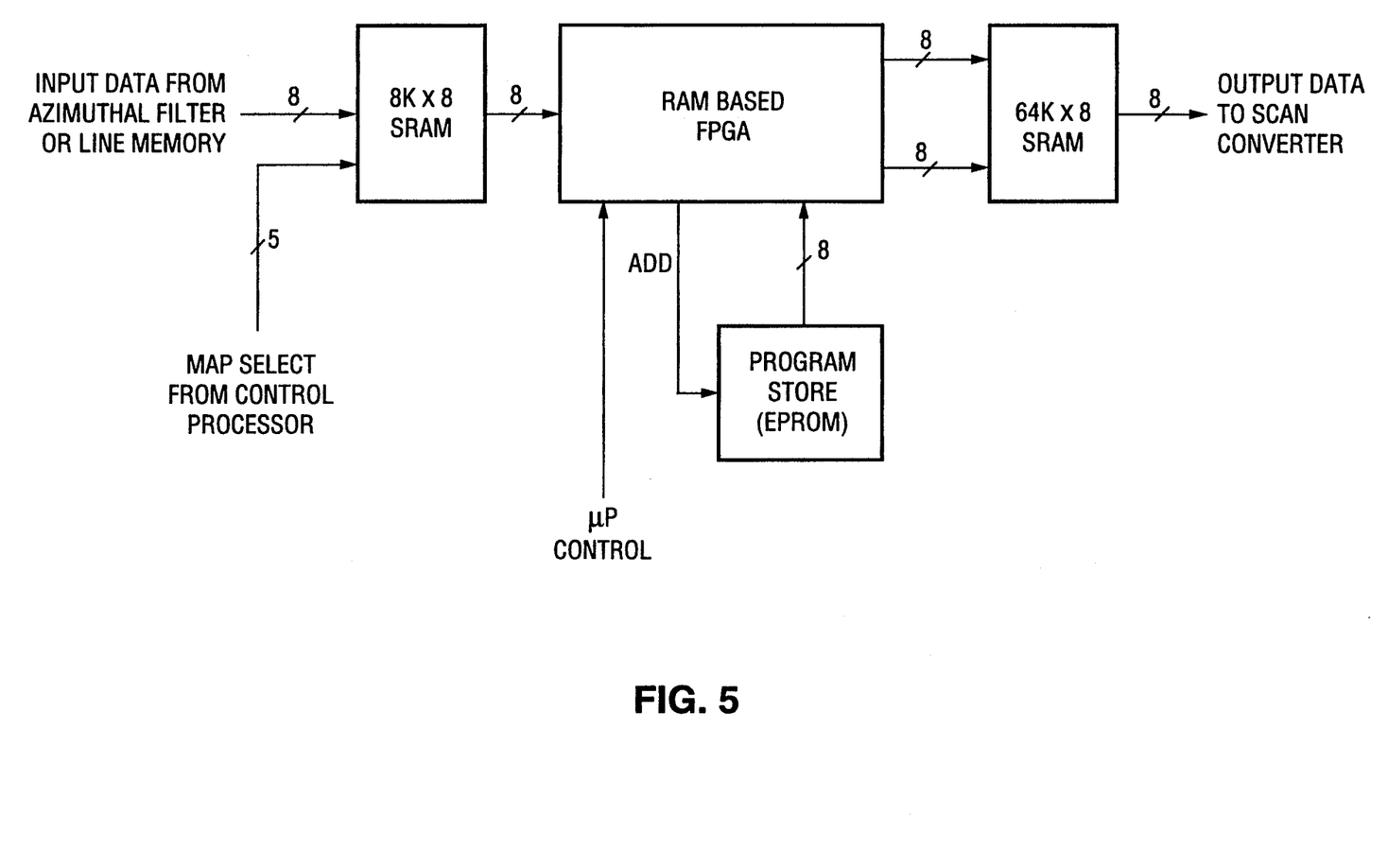
FIG. 5 is a simplified schematic diagram of the non-linear range filter of FIG. 4.

The more general digital range filter structure is shown in the functional block diagram of FIG. 4, which may be implemented with the digital circuit of FIG. 5. The filtered and digitized scan line data is first mapped through a nonlinear function 40 and then filtered using an FIR filter which can have both linear and nonlinear combining operations and an even or odd numbers of taps. The pre-summed outputs at summers 41 along with the signal on center tap 11 are mapped through a non-linear function 42 to the final digital output containing the filtered data.

Efficient digital circuit implementations of this filter are realized using RAM based look-up table memories for the nonlinear mapping functions. The parameter weightings required to maintain a constant DC gain dynamic filter are implicit in these mappings. Since the final non-linear combining operations are arbitrary non-linear functions, the data from inner and outer tap summations can be combined at 41 using a nonlinear operation 43 (e.g. RMS sum or maximum operations) followed by the arbitrary output mapping at 42.

With a RAM based programmable logic device implementation as indicated in FIG. 5, flexible filter topologies with different tap spacings and different combining structures can be implemented under program control. For example, a typical logic device program shown in FIG. 6 would implement the basic filter topology shown in FIG. 4. This type of architecture clearly permits a wide range of possibilities for flexible downloadable filtering algorithms, including an algorithm which closely duplicates the performance of one-dimensional dynamic non-linear analog filter structures of FIG. 2, 3. The data paths required for log compressed video processing are typically 8 bits at the input and output as shown in FIG. 5; however, more bits are accommodated by using larger tables.

Figure 6:
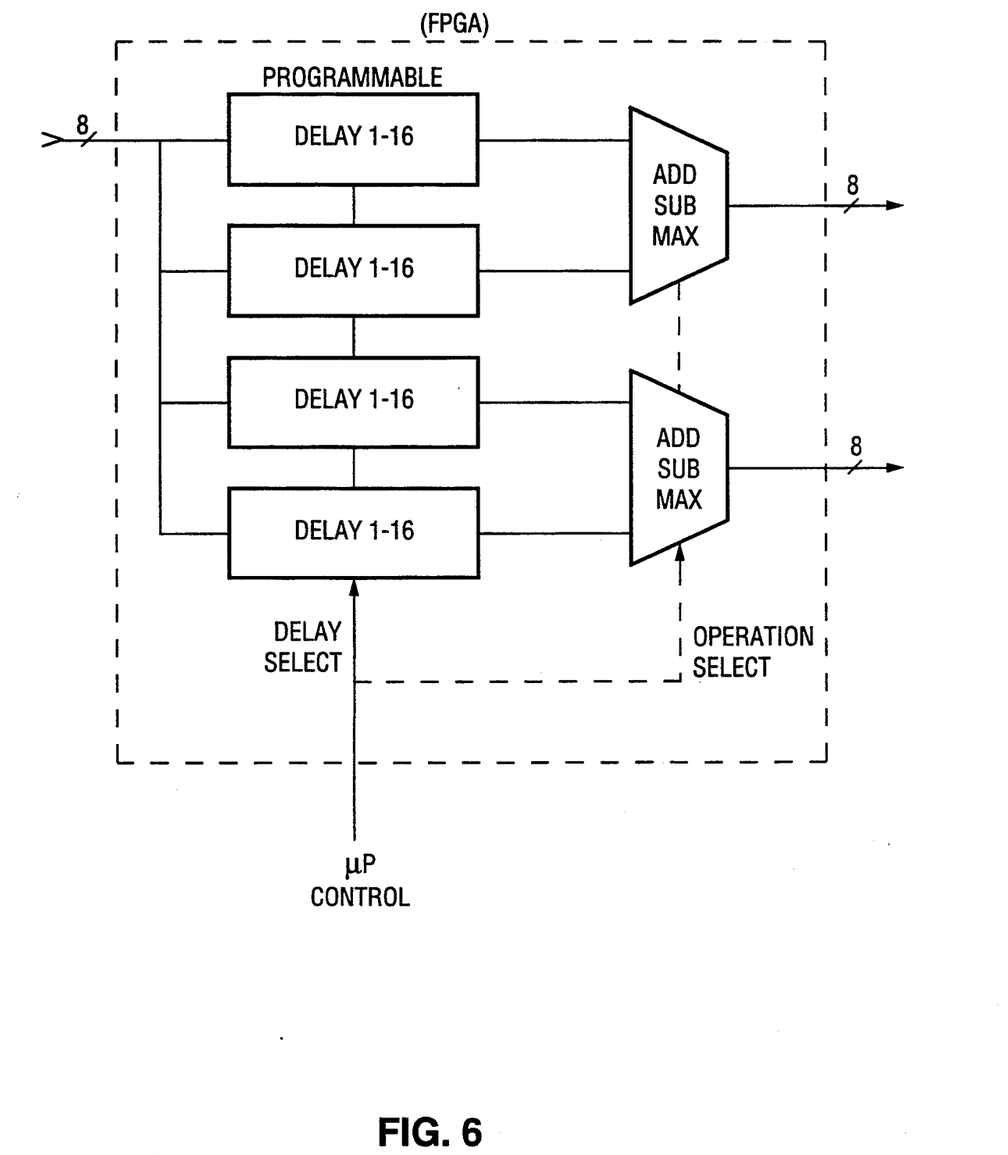
FIG. 6 is a typical programming model for the range filter FPGA of FIG. 5 for a four-tap non-linear range filter.

Innovations in the digital circuit of FIGS. 5, 6 include flexible digital implementation of dynamic non-linear range filters with the properties and benefits described; efficient and flexible methods for digitally combining terms in the dynamic feed forward nonlinear FIR structure using more general nonlinear combining operations (including for example RMS summation and maximum operations); a digital technique which allows implicit weighting and summing of the nonlinear FIR parameters in order to preserve the constant DC gain properties of the filter, when desired; a technique to allow accurate and instantaneous variation of the filter response under programming control applicable in both conventional and dynamic nonlinear modes; techniques which allow dynamic filter parameter control based on more general measures of the local signal characteristics; and a technique which efficiently incorporates nonlinear mappings of the data at the input and output of the filter.

Figure 7:
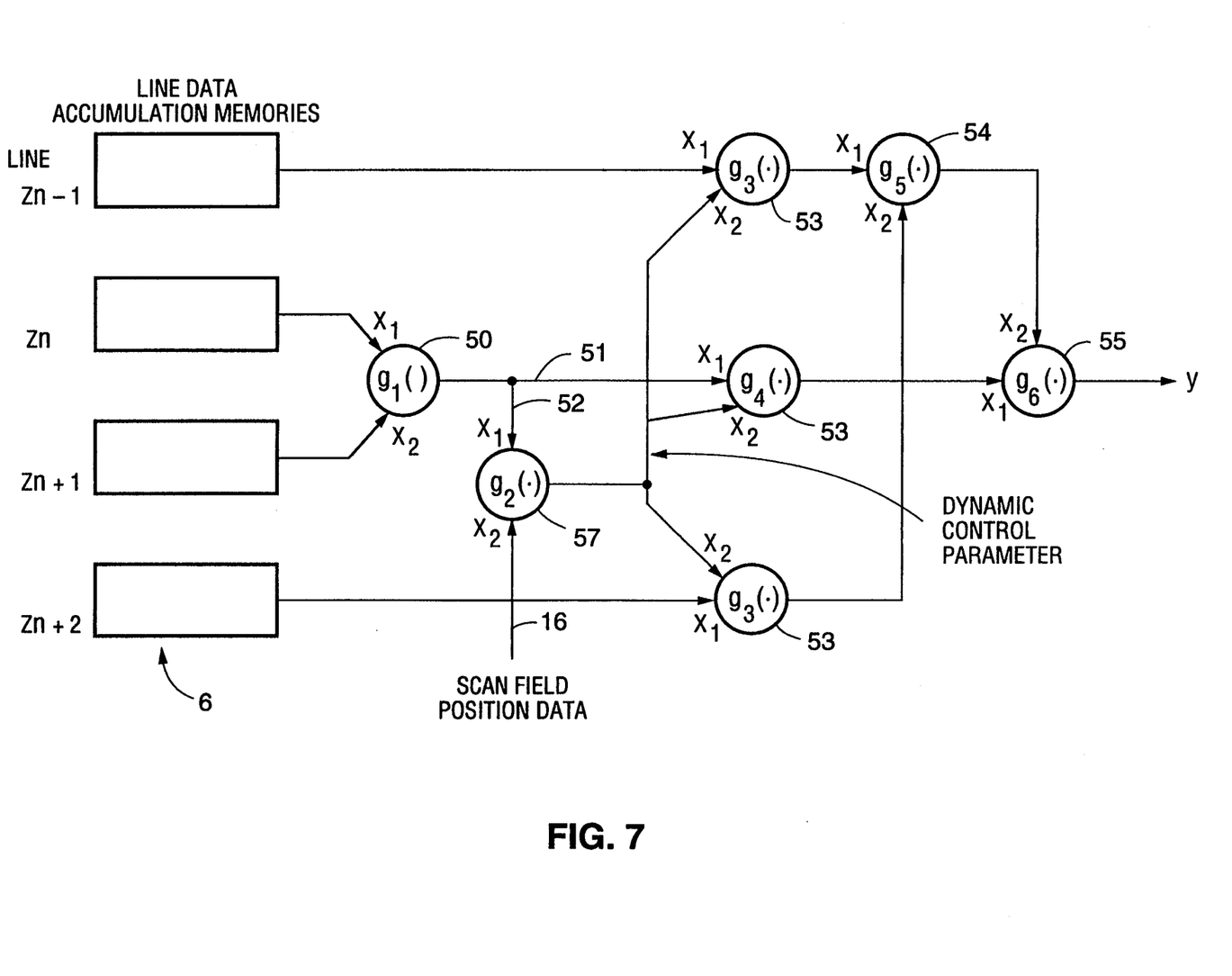
FIG. 7 is a functional block diagram for a non-linear azimuthal filter of this invention.

The general structure of the azimuthal dynamic non-linear filter is shown in FIG. 7. The filter combines samples in azimuth at each range from an even or odd number of acquired ultrasound lines (Zn−1, Zn, Zn−1, Zn+2) which are buffered in the line accumulation memory 6. The number of lines used and the line spacings are programmable over a relatively compact region in order to match different azimuthal spectral characteristics resulting from the transducer and system scanning parameters. If an even number of lines is chosen for the azimuth filter, the center line data terms are pre-combined using a programmable nonlinear combining operator 50. Programmed operations can include linear summation, RMS summation, min/max, or other nonlinear operations.

The structure of FIG. 7 shows a four line filter example. The pre-combined center lines are used for final output 51 combining with the outer lines and also as an input 52 to drive the nonlinear filter parameter control map 57. This nonlinear map generates the filter control parameter as a nonlinear function of combined center line intensity, line range, and line azimuth location in the scanning field at 16. Thus, the filter response is a spatially varying function of position within the scan field. This filter control parameter is used to map the combined center line value and two end line signal values at 53 prior to final combining. The final combining of inner and outer terms is implemented at 54, 55, respectively, with another programmable two variable non-linear operations. Programmed operations can include linear summation, RMS summation, min/max, or other nonlinear operations.

The availability of various nonlinear combining operations under the programmed control give this filter structure a powerful capability for dynamic nonlinear filtering with either linear or nonlinear tap data summations. For example, the azimuthal filter can implement a family of responses varying from low pass smoothing to high pass peaking responses as a function of increasing local signal level (similar to the one-dimensional nonlinear analog filter). This type of filter suppresses noise and reduces tissue contrast degradation in lower gray levels of the image while enhancing detail in brighter echoes. The programmability of filter order and azimuthal line spacings insure that several useful families of nonlinear responses can be generated.

Figure 8:
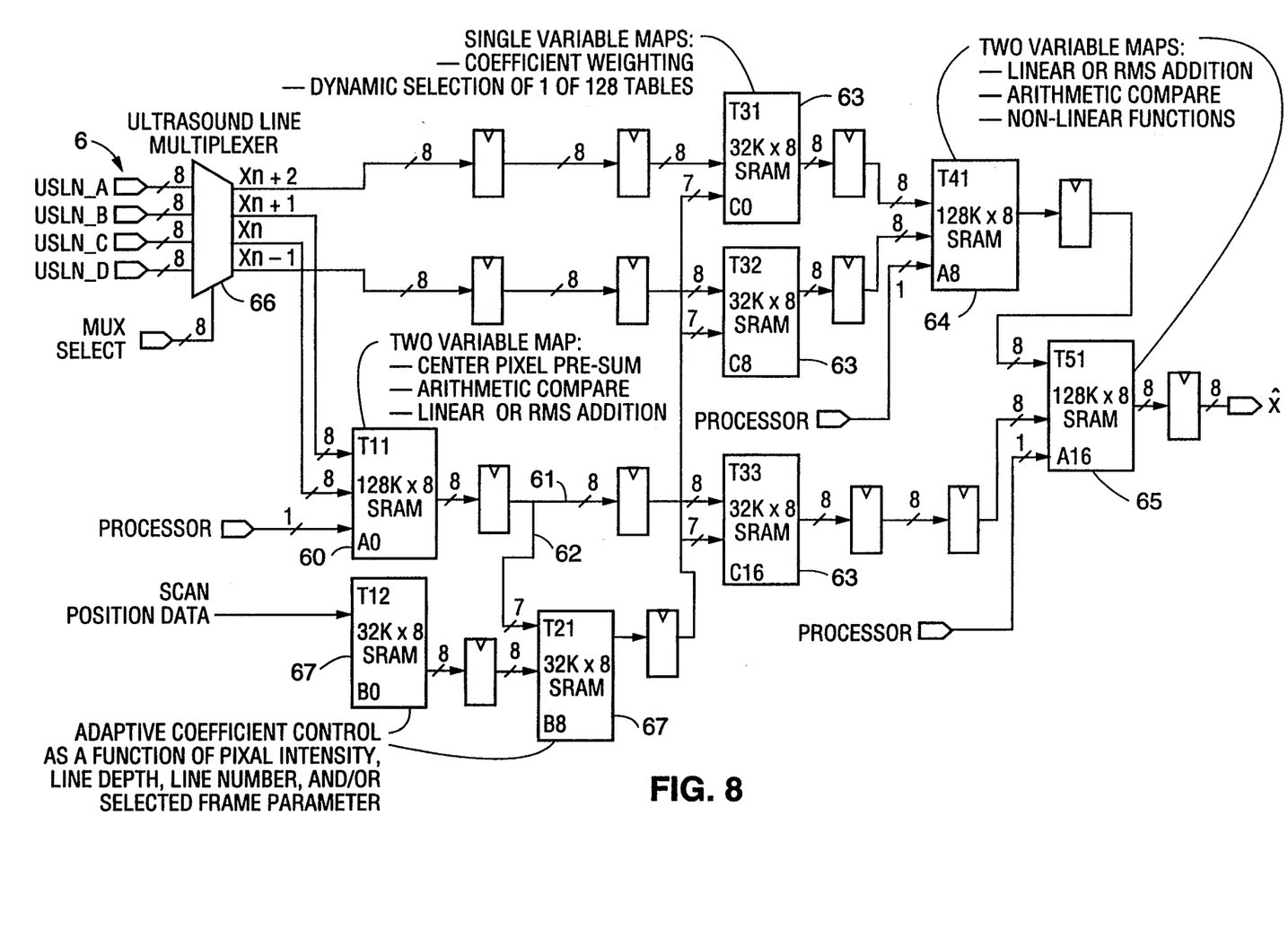
FIG. 8 is a simplified schematic diagram of the non-linear azimuthal filter of FIG. 7.

FIG. 8 shows the details of a digital implementation of the dynamic non-linear azimuthal filter. Static RAM based lookup tables 60, 63, 64, 65 implement the programmable nonlinear parameter generation and combining operations. A digital multiplexer 66, is used at the output of the line accumulation memories 6 to select a set of three or four line samples with spacings that match the objectives of the imaging mode. New nonlinear parameter generation operations can be downloaded at the same time a line selection mode is changed in order to optimize the response family. Spatially dependent and signal dependent filter parameter variation is achieved by a two variable look-up table map implemented in static RAM 67. In the filter circuit shown, all data and parameter control flow path delays are matched so that the filter response is essentially varying instantaneously with the signal.

Innovations in the digital circuit of FIG. 8 include a flexible digital architecture for implementing dynamic nonlinear azimuthal filters with the properties and benefits described; a flexible architecture for selecting groups of azimuthal line samples for parallel processing by the filter where the number of lines and sample spacing are programmable; an efficient and flexible architecture for digitally combining terms in the dynamic feed forward nonlinear FIR structure using more general nonlinear combining operations (including for example RMS summation and maximum operations) which can be paramaterized and driven by the signal to achieve instantaneous variation of the filter response; architecture which allows implicit weighting and summing of the parallel nonlinear FIR terms in order to control the response and average gain properties of the filter, when desired; an efficient and flexible method for spatially varying the filter parameters and control action based on range and azimuth location within the scanning field; and architecture for filter control which allows dynamic filter control based on more general measures of the local signal characteristics.

Variations of the described embodiments are apparent. Extensions of the analog filter could be constructed which would provide additional filtering flexibility and image enhancement capability. For example, FIR filter response families generated with more taps and with more than one parameter can be implemented by adding additional multiplexing switches and tap summing nodes, additional multipliers (one for each filter parameter), and additional nonlinear control circuits (also one for each filter). The nonlinear control circuits could be implemented using other than clipped linear weighting maps to achieve different mappings and different dynamic behaviors. The feed forward signal which drives the nonlinear filter controller could be derived as a symmetric weighted linear or nonlinear sum of delayed signals, representing alternative local measures of the image. These extensions involve expanding parts of the circuit which are shared with multiple programmable tap settings corresponding to multiple families of responses.

Alternative circuit technologies and topologies may also be useful to implement the analog nonlinear range filter. For example, integrated circuit filters with electronically controlled (voltage controlled) constant delay low pass and high pass filter sections have been developed for magnetic recording equalizer applications. These IC filter designs achieve bandwidths adequate for ultrasound video signal processing and provide a means for continuously varying the bandwidth without using passive delay lines. A disadvantage of these circuits, however, relative to the one described, is their relatively limited range of frequency response programmability.

For one-dimensional non-linear digital filtering extensions of the filtering capabilities described can be made by increasing the look-up table memory size and the capacity of the filter programmable logic device. Alternatively, the filter could be implemented with more conventional arithmetic processing circuits, for example with the parametric filter term combining and dynamic control accomplished using digital multipliers and/or other combinations of computational logic building blocks.

Two-dimensional non-linear filtering capability can be extended by increasing the number of lines involved in the filter and increasing the number and/or size of pre-summing and combining tables. The filter could also be implemented with more conventional arithmetic processing building blocks, but with likely restricted generality of the processing algorithms.

The dynamic nonlinear filtering technique has been described in the context of independent digital range and azimuth filter structures; however, the technique can be used productively in the context of a non separable 2-D FIR kernel based filter. Since the separable filters described are a subclass of this more general 2-D FIR kernel approach, the performance benefits are greater in this context. For example, sensitivity to image spatial orientation can be reduced. The dynamic nonlinear processing principle can be used for dynamic control of the 2-D kernel, resulting in a single (multiparameter) control path instead of separate ones for range and azimuth.

Figure 9:
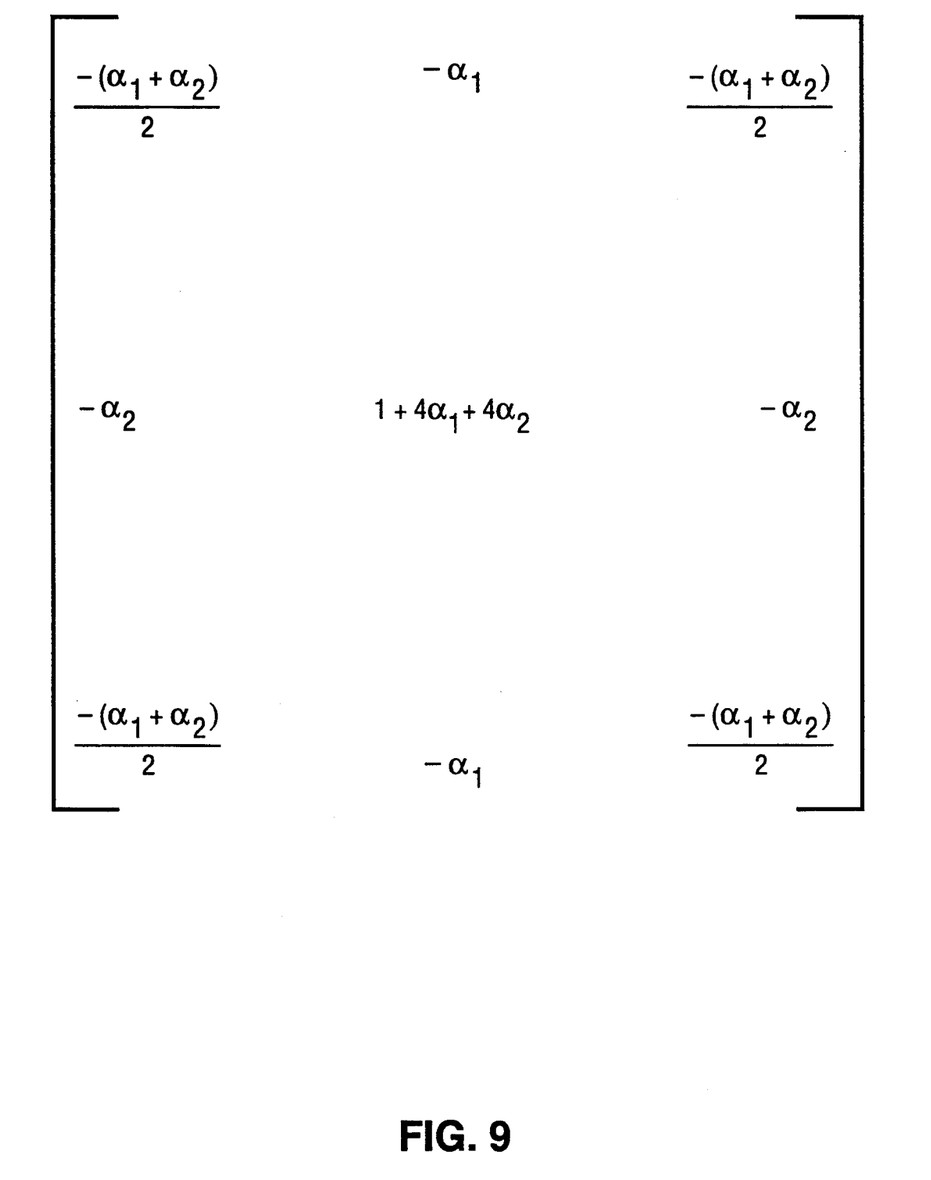
FIG. 9 is a schematic of a two parameter, non-linear two-dimensional non-separable filter kernel.

For example, consider the 3×3 linear FIR kernel defined in FIG. 9 The two parameters, $\alpha_1$, and $\alpha_2$ can be varied from negative values corresponding to a low pass smoothing kernel to positive values corresponding to a high pass sharpening kernel, while the DC gain remains constant. The dynamic nonlinear technique is applied by making these parameters programmable nonlinear functions of the local signal value. While the filter term combining operations in this example are linear summations, clearly nonlinear operations similar to those described already can also be used (i.e. a nonlinear FIR kernel.)

Figure 10:
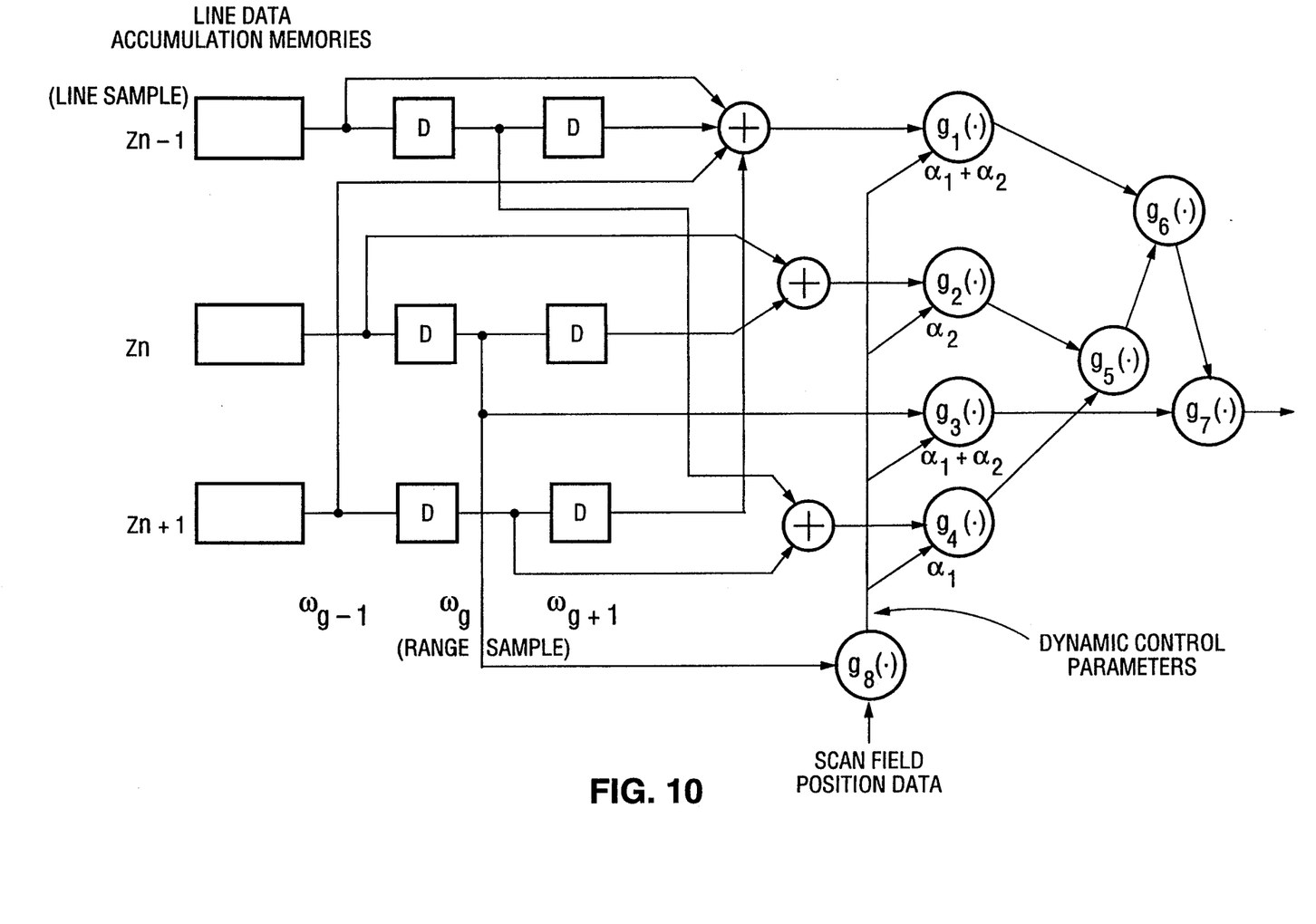
FIG. 10 is a schematic of a non-linear two-dimensional non-separable filter kernel.

The construction of an efficient digital circuit to perform the dynamic nonlinear processing in this context is shown in FIG. 10. Here the $\alpha_1$, and $\alpha_2$ terms of the kernel are pre-summed and the final output is obtained by combining the partial terms through a set of nonlinear look-up table based maps. The range and azimuth sample spacings representing the kernel span can be programmable as before along with the nonlinear dynamic control function in order to match the desired objectives of the transducer and system imaging mode.

A preferred embodiment described above talks about a family or set of filters that can be implemented for a particular probe or application. Since the architecture described in this disclosure allows for very fine control of the filter parameters, an even larger number of filters can be implemented where the difference between adjacent filters is much smaller than in the family described. A rotary control, or some other continuous switch means, can be used to select the filters. This control provides a sharpness control where a broad range of smoothing or sharpening alternatives are available to the user.

We claim:

1. Apparatus for enhancing the clarity of the diagnostic information in real-time B-mode and M-mode ultrasound displays comprising;

beamformer means for acquiring ultrasound receive signals for each ultrasound scan line of a two-dimensional image;

video processing means for converting the receive signals for each ultrasound scan line into detected video signals;

programmable non-linear spatial filter means for processing said video signals with continuously and automatically varying filter responses; and means for display of said filtered video signals.

2. The apparatus of claim 1 wherein the non-linear filter means processes said video signals in range along each ultrasound scan line.

3. The apparatus of claim 1 wherein the non-linear filter means processes said video signals azimuthally along multiple ultrasound scan lines of a two-dimensional B-mode image.

4. The apparatus of claim 1 wherein the non-linear filter means is two-dimensionally programmable for processing said video signals both in range along each ultrasound scan line and azimuthally along multiple ultrasound scan lines over a local region of a two-dimensional B-mode image.

5. The apparatus of claim 1 wherein the non-linear filter means is responsive to a local signal measurement for control of filter parameters.

6. The apparatus of claim 1 wherein the non-linear filter means is responsive to spatial positions in a B-mode image for control of filter parameters.

7. The apparatus of claim 1 wherein the non-linear filter means is programmable to accommodate variable system characteristics for particular imaging applications.

8. A method for enhancing the clarity of the diagnostic information in real-time B-mode and M-mode ultrasound displays comprising the steps of acquiring ultrasound receive signals for each ultrasound scan line of a two-dimensional image;

converting the receive signals for each ultrasound scan line into detected and filtered video signals;

non-linearly spatially filtering said video signals with continuously and automatically varying filter responses; and scan converting and displaying said filtered video signals.

9. The method of claim 8 wherein the non-linear filtering processes said video signals in range along each ultrasound scan line.

10. The method of claim 8 wherein the non-linear filtering processes said video signals azimuthally along multiple ultrasound scan lines of a two-dimensional B-mode image.

11. The method of claim 8 wherein the non-linear filtering is two-dimensionally programmable for processing said video signals both in range along each ultrasound scan line and azimuthally along multiple ultrasound scan lines over a local region of a two-dimensional B-mode image.

12. The method of claim 8 wherein the non-linear filtering is responsive to a local signal measurement for control of filter parameters.

13. The method of claim 8 wherein the non-linear filtering is responsive to spatial positions in a B-mode image for control of filter parameters.

14. The methods of claim 8 wherein the non-linear filtering is programmable to accommodate variable system characteristics for particular imaging applications.

* * * * *

UNITED STATES PATENT OFFICE
CERTIFICATE OF CORRECTION

Patent No. 5,396,285          Dated March 7, 1995

Inventor(s) Dave Hedberg et al

It is certified that error appears in the above-identified patent and that said Letters Patent is hereby corrected as shown below:

Col. 7, line 23; "$x(t\gamma)$" should be --- $x(t-\gamma)$ ---

Col. 7, line 52; after "input." and before "The" the following sentence should be added --- The gain-offset input value at 33' is also added to the saturation limit 33' in order to make the saturation level effectively constant. ---

Col. 8, line 36; after "at 41" add the following ---, or optionally at 43, ---

Col. 8, line 37; "43" should be deleted

Col. 8, line 37; after "operations)" delete "followed by" and insert --- and ---

Col. 9, line 8; "Zn-1" at its second occurrence should be --- Zn+1 ---

Signed and Sealed this

Eleventh Day of July, 1995

*Attest:*

BRUCE LEHMAN

*Attesting Officer*    *Commissioner of Patents and Trademarks*